United States Patent [19]
Krüger et al.

[11] Patent Number: 5,176,914
[45] Date of Patent: Jan. 5, 1993

[54] FUNGICIDAL CARBOCYCLIC ANILIDE CARBAMATES

[75] Inventors: Bernd-Wieland Krüger; Klaus Sasse, both of Bergisch-Gladbach; Wilhelm Brandes, Leichlingen, all of Fed. Rep. of Germany

[73] Assignee: Bayer Aktiengesellschaft, Leverkusen, Fed. Rep. of Germany

[21] Appl. No.: 568,459

[22] Filed: Aug. 15, 1990

[30] Foreign Application Priority Data

Sep. 2, 1989 [DE] Fed. Rep. of Germany ....... 3929232
Apr. 21, 1990 [DE] Fed. Rep. of Germany ....... 4012791

[51] Int. Cl.⁵ ................. A01N 25/00; A01N 47/10; C07C 211/00
[52] U.S. Cl. .................. 424/405; 514/480; 514/486; 514/490; 560/29; 560/32; 560/33; 560/133; 560/136; 560/145; 560/146
[58] Field of Search ............. 560/133, 136, 145, 146, 560/32, 33, 29; 514/490, 480, 486; 424/405

[56] References Cited

U.S. PATENT DOCUMENTS 4,051,254 9/1977 Maravetz ................ 424/285

FOREIGN PATENT DOCUMENTS 0116409 8/1984 European Pat. Off.
0293718 12/1988 European Pat. Off.

Primary Examiner—Jose G. Dees
Assistant Examiner—Porfirio Nazario
Attorney, Agent, or Firm—Sprung Horn Kramer & Woods

[57] ABSTRACT

Fungicidal carbocyclic anilide carbamates of the formula

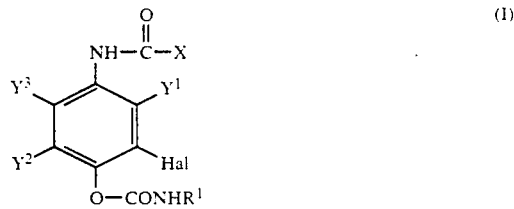

in which
X represents optionally alkyl-substituted cycloalkyl or optionally alkyl-substituted cycloalkenyl,
Hal represents halogen, and
$Y^1$, $Y^2$ and $Y^3$ independently of one another represent hydrogen, halogen, optionally halogen-substituted alkyl, optionally halogen-substituted alkoxy or optionally halogen-substituted alkylthio, and
$R^1$ represents optionally halogen-substituted alkyl, alkenyl, alkylcarbonyloxyalkyl, alkenylcarbonyloxyalkyl and optionally substituted cycloalkyl which can be interrupted by hetero atoms, or represents optionally substituted phenyl or optionally substituted phenylalkyl, or $R^1$ additionally can represent alkoxyalkyl, alkylthioalkyl or polyalkoxyalkyl if X represents optionally alkyl-substituted cycloalkenyl.

22 Claims, No Drawings

FUNGICIDAL CARBOCYCLIC ANILIDE CARBAMATES

The present invention relates to new cycloalkyl- or cycloalkenylcarboxanilide carbamates, to a process for their preparation, and to their use for combating pests, in particular fungi.

It is known that certain substituted 3-aminophenyl-carbamates have herbicidal properties (cf. U.S. Pat. No. 3,832,384).

Furthermore, many phenylcarbamates having a fungicidal action are known (cf. EP 116,409; EP 117,024; EP 125,901 and EP 293,718).

Furthermore, many carboxanilides having a fungicidal action, in particular having an action against benzimidazole-tolerant phytopathogens, are known (cf. Ep 100,615).

New cycloalkyl or cycloalkenyl-carboxanilide carbamates of the general formula (I)

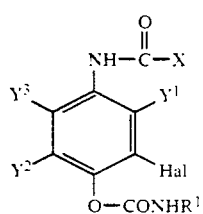

have been found, in which formula
- X represents optionally alkyl-substituted cycloalkyl or optionally alkyl-substituted cycloalkenyl,
- Hal represents halogen, and
- $Y^1$, $Y^2$ and $Y^3$ independently of one another represent hydrogen, halogen, optionally halogen-substituted alkyl, optionally halogen-substituted alkoxy or optionally halogen-substituted alkylthio, and
- $R^1$ represents optionally halogen-substituted alkyl, alkenyl, alkylcarbonyloxyalkyl, alkenylcarbonyloxyalkyl and optionally substituted cycloalkyl which can be interrupted by hetero atoms, or represents optionally substituted phenyl and optionally substituted phenylalkyl, and $R^1$ additionally can represent alkoxyalkyl, alkylthioalkyl or polyalkoxyalkyl if X represents optionally alkyl-substituted cycloalkenyl.

The substituted cycloalkyl- or cycloalkenylcarboxanilide carbamates of the formula (I) contain one or more centers of asymmetry and can therefore be present in the form of diastereomers or mixtures of diastereomers, which are obtained in various ratios. They are mainly obtained in the form of racemates.

Furthermore, it has been found that the new substituted cycloalkyl- or cycloalkenylcarboxanilide carbamates of the formula (I)

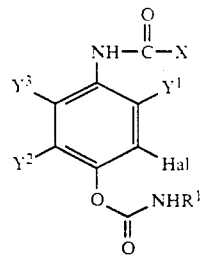

in which
- X represents optionally alkyl-substituted cycloalkyl or optionally alkyl-substituted cycloalkenyl,
- Hal represents halogen, and
- $Y^1$, $Y^2$ and $Y^3$ are identical or different and represent hydrogen, halogen, optionally halogen-substituted alkyl, optionally halogen-substituted alkoxy or optionally halogen-substituted alkylthio, and
- $R^1$ represents optionally halogen-substituted alkyl, alkenyl, alkylcarbonyloxyalkyl, alkenylcarbonyloxyalkyl and optionally substituted cycloalkyl which can be interrupted by hetero atoms, or represents optionally substituted phenyl and optionally substituted phenylalkyl, and $R^1$ additionally can represent alkoxyalkyl, alkylthioalkyl or polyalkoxyalkyl if X represents optionally alkyl-substituted cycloalkenyl, are obtained when aminophenols of the formula (II)

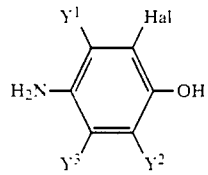

in which
- Hal, $Y^1$, $Y^2$ and $Y^3$ have the abovementioned meanings, are reacted, in a first reaction step, with carboxylic acid derivatives of the formula (III)

in which
- X has the abovementioned meaning and
- $Hal^1$ represents halogen, preferably chlorine, or a leaving group customary in acylation reactions, preferably an activating ester radical, if appropriate in the presence of an acid acceptor and if appropriate in the presence of a solvent or diluent, and in a second reaction step, the resulting intermediates of the formula (IV)

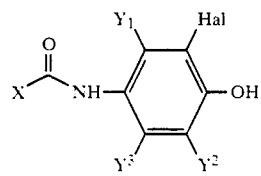

in which X, $Y^1$, $Y^2$, $Y^3$ and Hal have the abovementioned meanings, are then reacted with isocyanates of the formula (V)

$$R^1\text{—NCO} \qquad (V)$$

in which $R^1$ has the abovementioned meaning, if appropriate in the presence of a base and if appropriate in the presence of solvents or diluents.

Finally, it has been found that the substituted cycloalkyl- or cycloalkenyl-carboxanilide carbamates of the formula (I) have, inter alia, a high fungicidal activity. The new compounds can also be used in synergistic mixtures with other known, highly active compounds Within the scope of the present invention, the substituents preferably have the following meanings:

Unless stated otherwise, halogen can be fluorine, chlorine, bromine and iodine, preferably fluorine, chlorine and bromine.

Alkyl, alkoxy, alkoxyalkyl, polyalkoxyalkyl, alkylthio and alkylthioalkyl represent a radial having 1–8, preferably 1–6 and particularly preferably 1–4, carbon atoms per alkyl unit, for example methyl, ethyl, n- and iso-propyl, n-, sec-, iso- and tert.-butyl, pentyl, n-hexyl or iso-hexyl, methoxy, ethoxy, n- and iso-propoxy, n-, sec-, iso- and tert.-butoxy, pentoxy and hexoxy, methylthio, ethylthio, n- and iso-propylthio, n-, sec-, iso- and tert.-butylthio, pentylthio and hexylthio.

Halogenoalkoxy or halogenoalkylthio generally represents a straight-chain or branched hydrocarbon radical which has 1–6 carbon atoms and 1–9 identical or different halogen atoms and which is linked via oxygen or sulphur, respectively. Preferred radicals are those having 1–4 carbon atoms and 1–5 identical or different halogen atoms. Very particularly preferred radicals are those having 1 or 2 carbon atoms and 1–3 identical or different halogen atoms. The following may be mentioned as examples: trifluoromethoxy, trichloromethoxy, difluorochloromethoxy, dichlorofluoromethoxy, difluoroethoxy, trifluoroethoxy, tetrafluoroethoxy, pentafluoroethoxy, trifluoromethylthio, trichloromethylthio, difluorochloromethylthio, dichlorofluoromethylthio, difluoroethylthio, trifluoromethylthio and tetrafluoroethylthio.

Halogenoalkyl has the meaning of halogenoalkoxy with the difference that the oxygen or sulphur atom is missing.

Cycloalkyl generally represents a cyclic hydrocarbon radical having 3–10 carbon atoms. Preferred radicals are those having 3–7 carbon atoms. The following may be mentioned as examples: cyclopropyl, cyclobutyl, cyclopentyl, cyclohexyl, cycloheptyl and cyclodecanyl.

The cycloalkyl radicals can be monosubstituted to polysubstituted. Substituents which may be mentioned are alkyl having 1–4 carbon atoms, halogen and alkoxy having 1–4 carbon atoms.

Cycloalkenyl generally represents a cyclic hydrocarbon radical having 5–10 carbon atoms.

Preferred radicals are those having 5–7 carbon atoms. The following may be mentioned as examples: cyclopentenyl, cyclohexenyl and cycloheptenyl.

The cycloalkenyl radicals can be monosubstituted to polysubstituted. Substituents which may be mentioned are alkyl radicals having 1–6 carbon atoms.

Alkyl in this context has the preferred and particularly preferred meaning which has already been mentioned further above.

Phenyl and phenylalkyl generally represent phenyl and phenylalkyl in which phenyl hydrogen atoms are optionally substituted by one or more substituents $Y^1{}'-Y^5{}'$. $Y^1{}'-Y^5{}'$ in this context have the meaning of $Y^1$, $Y^2$ and $Y^3$, and also nitro and cyano.

Alkenyl generally represents a straight-chain or branched hydrocarbon radical having 2 to 8 carbon atoms and one or more, preferably one or two, double bonds. Lower alkenyl having 2 to 6 carbon atoms and one double bond is preferred. An alkenyl radical having 2 to 5 carbon atoms and one double bond is particularly preferred.

Formula (I) provides a general definition of the substituted cycloalkyl- or cycloalkenyl-carboxanilides according to e invention. Preferred compounds of the formula (I) are those where X represents cyclopropyl, cyclobutyl, cyclopentyl, cyclohexyl or cycloheptyl, each of which is optionally monosubstituted to hexasubstituted by identical or different substituents from the series comprising straight-chain or branched alkyl radicals having 1–4 carbon atoms, or represents cycloalkenyl having 5–7 ring members where the cycloalkenyl radical can be monosubstituted to hexasubstituted by identical or different substituents from the series comprising straight-chain or branched alkyl radicals having 1–4 carbon atoms.

Hal represents fluorine, chlorine or bromine.

$Y^1$, $Y^2$ and $Y^3$ are identical or different and represent hydrogen, fluorine, chlorine, bromine, straight-chain or branched alkyl having 1–4 carbon atoms, straight-chain or branched alkoxy or alkylthio each having 1–4 carbon atoms, or represent halogenoalkyl, halogenoalkoxy or halogenoalkylthio each having 1–4 carbon atoms in the straight-chain or branched alkyl moiety and 1–5 identical or different halogen atoms, and R represents $C_1$–$C_8$-alkyl, $C_2$–$C_8$-alkenyl, $C_1$–$C_8$-alkylcarbonyloxy-$C_1$–$C_6$-alkyl or $C_2$–$C_8$-alkenylcarbonyloxy-$C_1$–$C_6$-alkyl, each of which is unsubstituted or monosubstituted to nonasubstituted by halogen, or represents $C_3$–$C_7$-cycloalkyl which is unsubstituted or monosubstituted to pentasubstituted by identical or different substituents from the series comprising halogen, $C_1$–$C_4$-alkyl or $C_1$–$C_4$-alkoxy, or represents phenyl which is unsubstituted or monosubstituted to pentasubstituted by identical or different substituents from the series comprising $Y^1{}'$–$Y^5{}'$, or represents phenyl-$C_1$–$C_4$-alkyl which is unsubstituted or monosubstituted to pentasubstituted in the phenyl moiety by identical or different substituents from the series comprising $Y^1{}'$–$Y^5{}'$, where $Y^1{}'$–$Y^5{}'$ are identical or different and have the meaning of $Y^1$–$Y^3$, $NO_2$ and cyano, or $R^1$ additionally can represent $C_1$–$C_4$-alkoxy-$C_1$–$C_4$-alkyl, $C_1$–$C_8$-alkylthio-$C_1$–$C_8$-alkyl or $C_1$–$C_4$-alkoxy-$C_1$–$C_4$-alkoxy-$C_1$–$C_4$-alkyl if X represents optionally $C_1$–$C_4$-alkyl-substituted cycloalkenyl having 5–7 ring members.

Particularly preferred compounds of the formula (I) are those where

X represents cyclopropyl, cyclobutyl, cyclopentyl, cyclohexyl or cycloheptyl, each of which is monosubstituted or disubstituted by identical or different substituents from the series comprising straight-chain or branched alkyl radicals having 1–4 carbon atoms, or represents cyclopentenyl, cyclohexenyl or cycloheptenyl, each of which is optionally monosubstituted or disubstituted by identical or different substituents from the series comprising straight-chain or branched alkyl radicals having 1-4 carbon atoms, $Y^1$, $Y^2$ and $Y^3$ are identical or different and represent hydrogen, fluorine, chlorine, bromine, methyl or trifluoromethyl, and Hal represents fluorine, chlorine or bromine, and $R^1$ represents $C_1-C_6$-alkyl, $C_2-C_6$-alkenyl, $C_1-C_6$-alkylcarbonyloxy-$C_1-C_6$-alkyl or $C_2-C_6$-alkenylcarbonyloxy-$C_1-C_6$-alkyl, or $R^1$ additionally can represent $C_1-C_4$-alkoxy-$C_1-C_4$-alkyl, $C_1-C_6$-alkylthio-$C_1-C_6$-alkyl or $C_1-C_4$-alkoxy-$C_1-C_4$-alkoxy-$C_1-C_4$-alkyl if X represents in each case optionally methyl-substituted cyclopentenyl, cyclohexenyl or cycloheptenyl.

Very particularly preferred compounds of the formula (I) are those where

X represents cyclopentyl, cyclohexyl, cycloheptyl, cyclopentenyl, cyclohexenyl or cycloheptenyl, each of which is substituted in the 1- or 1,3-position by methyl or ethyl, and each of which is optionally additionally substituted by a further alkyl radical having 1-3 carbon atoms, Hal represents fluorine, chlorine or bromine, $Y^1$, $Y^2$ and $Y^3$ are identical or different and represent hydrogen, fluorine, chlorine, bromine or trifluoromethyl, and $R^1$ represents $C_1-C_4$-alkyl, $C_2-C_5$-alkenyl or $C_1-C_5$-alkylcarbonyloxy-$C_1-C_5$-alkyl, or $R^1$ additionally can represent $C_1-C_4$-alkoxy-$C_1-C_4$-alkyl, $C_1-C_4$-alkylthio-$C_1-C_4$-alkyl or $C_1-C_4$-alkoxy-$C_1-C_4$-alkoxy-$C_1-C_4$-alkyl if X represents in each case optionally 1-methyl- or 1,3-dimethyl-substituted cyclopentenyl, cyclohexenyl or cycloheptenyl.

If, for example, 2,6-dichloro-4-amino-phenol, 1-methyl-1-chlorocarbonylcyclohexane and 3-acetyl-oxypropyl isocyanate are used as starting substances, the course of the reaction can be represented by the following equation:

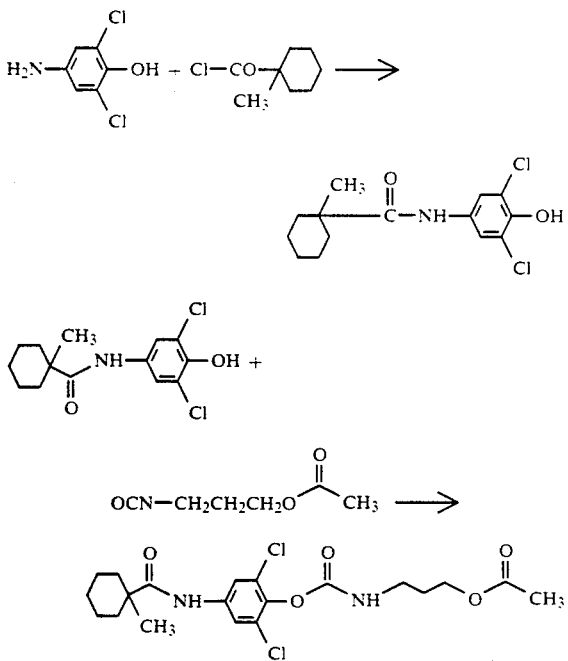

Formula (II) provides a general definition of the aminophenols required as starting substances for carrying out the process according to the invention. In this formula (II), the radicals Hal and $Y^1-Y^3$ have the meanings already given in connection with the description of the compounds of the formula (I) according to the invention. Most of the compounds are known and can be prepared by analogous processes (cf. "Methoden der organischen Chemie" [Methods of Organic Chemistry], Houben-Weyl, Vol. VI/1c, Phenols, Part 1, Georg Thieme Verlag, Stuttgart, 1976, and "Reaktionen der organischen Synthese" [Reactions in Organic Synthesis], Cesare Ferri, p. 81, 89, 91, 97, 118, 120, 122, 124, 126, 128, Georg Thieme Verlag, Stuttgart, 1978).

The 4-amino-2-chloro- or -2-bromo-6-trifluoromethylphenols are known from Jp. Kokai Tokkyo Koho Jp 61/126,055 and, for example, 4-amino-2,3,5,6-tetrafluorophenol from Zh. Org. Khim. 10(9), 1923–1927 (1974). The compounds of the formula (II A)

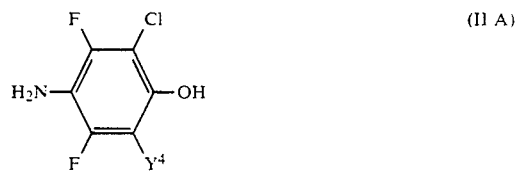

in which $Y^4$ represents fluorine or chlorine, are a subject of EP-A-293,718, and they can be prepared, for example, from corresponding hydroxybenzoic acids of the formula (VA)

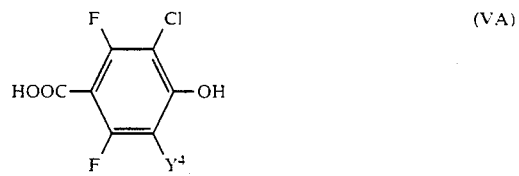

by decarboxylation, followed by nitration of the resulting phenols of the formulae (VI A)

to give the nitro compounds of the formula (VII A)

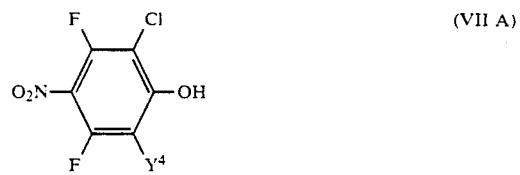

which are then hydrogenated, for example using hydrogen and Raney nickel, to give the corresponding amines of the formulae (II A).

The compounds of the formulae (VII A) are likewise a subject of EP-A-293,718.

Formula (III) in which X represents cycloalkyl or cycloalkenyl provides a general definition of the cycloalkanecarboxylic acid derivatives, or cycloalkenecarboxylic acid derivatives, respectively, furthermore required for carrying out the process according to the invention. In this formula (III), the radicals X' and Hal¹ have the meanings already given in connection with the description of the compounds of the formula (I) according to the invention. The compounds are known and can prepared by analogous processes (cf. Diversi et al., Synthesis 1971, 258; U.S. Pat. No. 3,674,831; "Reaktionen der organischen Synthese" [Reactions in Organic Synthesis] Cesare Ferri, p. 460, 461, 1978, Georg Thieme Verlag, Stuttgart; Houben-Weyl, Methoden der organischen Chemie [Methods of Organic Chemistry], Vol. 5 Pt. 1, p. 211, 320, 343, 428 et seq., C. Thieme-Verlag, Stuttgart, 1985).

The isocyanates in which R¹ has the abovementioned meaning and which are furthermore required for carrying out the process according to the invention, are known or can be prepared by analogous processes (cf. Methoden der organischen Chemie [Methods of Organic Chemistry], Houben-Weyl, Vol. E4, Carbonic Acid Derivatives, Georg Thieme Verlag, Stuttgart, p. 738 et seq. (1983)).

Formula (IV) provides a definition of the acylaminophenols used as intermediates in the process according to the invention.

Some of the compounds of the formula (IV) are new and are claimed in a parallel application.

The acylamino derivatives of the formula (IV) are obtained by reacting aminophenols of the formula (II)

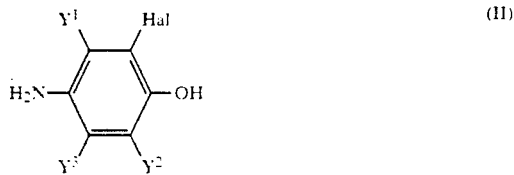

in which $Y^1$, $Y^2$, $Y^3$ and Hal have the abovementioned meanings, with carboxylic acid derivatives of the formula (III)

in which X' and Hal¹ have the abovementioned meanings, if appropriate in the presence of a solvent and if appropriate in the presence of an acid acceptor.

If appropriate, the process according to the invention is carried out in the presence of acid acceptors or bases. Acid acceptors which can be used are all customary acid-binding agents. The following have proven particularly useful: alkali metal carbonates and alkali metal alcoholates, such as sodium carbonate, potassium carbonate, sodium methylate, potassium methylate, sodium ethylate and potassium ethylate, furthermore aliphatic, aromatic and heterocyclic amines, for example triethylamine, trimethylamine, dimethylaniline, 1,8-diazabicyclo-(5,4,0)-undec-7-ene, dimethylbenzylamine and pyridine.

For carrying out the process according to the invention, 1-2 moles, in particular 1-1.4 moles, of the compounds of the general formula (III) are preferably employed per mole of aminophenol of the general formula (II), in the first reaction step.

In the second reaction step of the process according to the invention, 1-2 moles, in particular 1-1.4 moles, of the compounds of the general formula (V) are preferably employed per mole of acylaminophenol of the formula (IV).

Suitable diluents for carrying out the process according to the invention are virtually all inert organic diluents. These include, in particular, aliphatic and aromatic, optionally halogenated hydrocarbons, such as pentane, hexane, heptane, cyclohexane, petroleum ether, benzine, ligroin, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethyl phosphoric triamide.

In general, the process according to the invention is carried out at temperatures of between −50° C. and 120° C. The range between 0° C. and 110° C. is preferred. In general, the reactions are carried out under atmospheric pressure.

Working-up is carried out by customary methods, for example by extracting the products with toluene or methylene chloride from the reaction mixture which is diluted with water, washing the organic phase with water, drying and distilling, or so-called "incipient distillation", that is to say, prolonged heating to moderately increased temperatures under reduced pressure in order to free the product from the last volatile constituents, or by chromatographic purification over silica gel, or, for example, by crystallization. The compounds are characterized by the refractive index, melting point, $R_f$ value or boiling point.

The active compounds according to the invention are suitable for use for combating pests, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating Botrytis fungi on beans and for combating rice diseases, such as, for example, against the pathogen causing rice blast disease (*Pyricularia oryzae*).

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents can, for example, also used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol orglycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenohydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

EXAMPLE 1

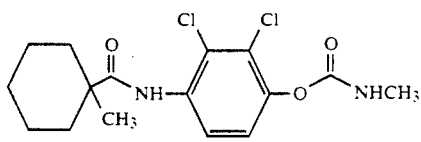

4 g (13.0 mmol) of 2,3-dichloro-4-(1-methylcyclohexyl-carbonylamino)-phenol are dissolved in 20 ml of toluene, and 0.9 g (19.5 mmol) of methyl isocyanate are added to the mixture at between 10° and 20° C. 30 mg of DBU (1,8-diazabicyclo-(5,4,0)-undec-7-ene) are subsequently added to the reaction mixture. The mixture is stirred for 2 hours at 20° C., and 1.0 g (21.7 mmol) of methyl isocyanate are added. When the reaction is complete (DC check), the mixture is cooled, and n-hexane is added slowly. The solid which has precipitated is filtered off with suction and washed with hexane. Yield: 3.5 g (81% of theory). M.P. 140° C.

The following compounds of the formula (I) are prepared analogously to Example 1:

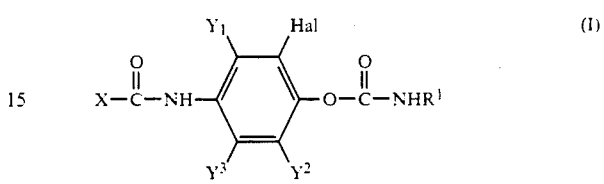

| Example No. | X | $Y^1$ | $Y^3$ | $Y^2$ | Hal | $R^1$ | Physical data m.p. |
|---|---|---|---|---|---|---|---|
| 2 | cyclohexyl-CH₃ | Cl | H | H | Cl | CH₂C(CH₃)₃ | 121° C. |
| 3 | cyclohexyl-CH₃ | Cl | H | H | Cl | C(CH₃)₃ | 118° C. |
| 4 | cyclohexyl-CH₃ | H | H | Cl | Cl | C(CH₃)₃ | 131° C. |
| 5 | cyclohexyl-CH₃ | H | H | Cl | Cl | CH₂C(CH₃)₃ | 140° C. |
| 6 | cyclohexyl-CH₃ | H | H | Cl | Cl | CH₂C(CH₃)₂CH₂OCOCH₃ | 35° C. |
| 7 | cyclohexyl-CH₃ | H | H | Cl | Cl | CH₂CH(CH₃)OCOCH₃ | 93° C. |
| 8 | cyclohexyl-CH₃ | H | H | Cl | Cl | CH₂CH(CH₃)OCOC₄H₉-t | 106° C. |
| 9 | cyclohexyl-CH₃ | H | H | Cl | Cl | CH₂C(CH₃)₂CH₂OCOC₄H₉-t | 38° C. |
| 10 | cyclohexyl-CH₃ | H | H | Cl | Cl | CH₂CH₂OCOC₄H₉-t | 132° C. |

-continued

| Example No. | X | Y¹ | Y³ | Y² | Hal | R¹ | Physical data m.p. |
|---|---|---|---|---|---|---|---|
| 11 | 1,1-dimethylcyclohexyl | H | H | Cl | Cl | $CH_2CH_2OCOCH_3$ | 119° C. |
| 12 | 1,1-dimethylcyclohexyl | Cl | H | H | Cl | $CH_2CH(CH_3)OCOC_4H_9\text{-}t$ | 103° C. |
| 13 | 1,1-dimethylcyclohexyl | Cl | H | H | Cl | $CH_2C(CH_3)_2CH_2OCOC_4H_9\text{-}t$ | 92° C. |
| 14 | 1,1-dimethylcyclohexyl | Cl | H | H | Cl | $CH_2CH_2OCOC_4H_9\text{-}t$ | 125° C. |
| 15 | 1,1-dimethylcyclohex-3-enyl | Cl | H | H | Cl | $CH_3$ | |
| 16 | 1,1,3-trimethylcyclohex-3-enyl | Cl | H | H | Cl | $CH_3$ | |
| 17 | 1,2,4-trimethylcyclohex-2-enyl | Cl | H | H | Cl | $CH_3$ | |
| 18 | 1,1,3-trimethylcyclohexyl | Cl | H | H | Cl | $CH_3$ | |
| 19 | 1,1,2,4-tetramethylcyclohexyl | Cl | H | H | Cl | $CH_3$ | |
| 20 | 1,1-dimethylcyclohexyl | F | F | F | Cl | $CH_3$ | |
| 21 | 1,1-dimethylcyclohexyl | H | H | Cl | Cl | 2,6-difluorophenyl | |

-continued

| Example No. | X | Y¹ | Y³ | Y² | Hal | R¹ | Physical data m.p. |
|---|---|---|---|---|---|---|---|
| 22 | ![cyclohexyl-CH3] | H | H | Cl | Cl | ![methoxy-methylphenyl] | |

PREPARATION EXAMPLES

Preparation of the Starting Compounds

EXAMPLE A1

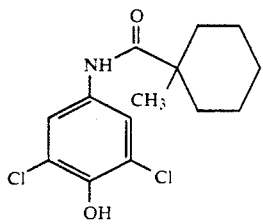

18.5 g (0.085 mol) of 4-amino-2,6-dichlorophenol are dissolved in 150 ml of tetrahydrofuran, and first 8.6 g (0.085 mol) of triethylamine and then, at 0° C. internal temperature, 15 g (0.094 mol) of 1-methylcyclohexanecarboxylic acid chloride are added. The mixture is stirred overnight at 20° C., and then another 5 g of carboxylic acid chloride and 2.8 g of triethylamine are then added to the reaction mixture to complete the reaction. After 2 hours, the mixture is poured onto ice, and the solid which has been filtered off with suction is recrystallized from toluene. This gives the abovementioned compound of melting point 140° C.; yield: 22.3 g (=87% of theory).

EXAMPLE A2

3,5-Dichloro-2,6-difluoro-4-hydroxybenzoic acid 300 g of potassium hydroxide, 600 ml of water, 15 g of tetrabutylammonium chloride and 135 g of 3,5-dichloro-2,4,6-trifluorobenzotrifluoride are initially introduced into a stirred vessel, and the mixture is then refluxed for 5 hours. When the reaction has finished, the mixture is cooled and rendered acid by dropwise addition of hydrochloric acid. The solid product is filtered off with suction and dried in vacuo. Yield: 93 g of melting point 102°-105° C.

EXAMPLE A3

3-Chloro-2,5,6-trifluoro-4-hydroxy-benzoic acid

Analogously to Example A2, 400 g of NaOH, 1,200 ml of water, 15 g of tetraethylammonium chloride and 276 g of 3-chloro-tetrafluorobenzotrifluoride, refluxed for 6 hours, give 238 g of product of a melting point of 87°-90° C.

EXAMPLE A4

2,6-Dichloro-3,5-difluorophenol 50 g of 3,5-dichloro-2,6-difluoro-4-hydroxybenzoic acid and 10 ml of dimethylformamide are mixed, and the mixture is heated. At 105°-130° C., carbon dioxide is evolved, and the mixture is allowed to react at this temperature until the reaction is complete. 200 ml of toluene and then 80 ml of water are subsequently stirred into the mixture, the phases are separated, and the organic phase is dried and subsequently distilled. This gives 34 g of the product having a boiling point of 87°-88° C. and a refractive index of $n_D^{20}$: 1.5310.

EXAMPLE A5

Analogously to Example A4, 2-chloro-3,5,6-trifluorophenol is obtained, having a boiling point of 68°-70° C./20 mbar.

EXAMPLE A6

2,6-Dichloro-3,5-difluoro-4-nitro-phenol 20 g of 2,6-dichloro-3,5-difluorophenol are initially introduced into 70 ml of acetic acid, and 8 g of 98% strength nitric acid are added dropwise. Stirring is subsequently continued for 2 hours at room temperature, and the mixture is taken up in 150 ml of dichloromethane and washed twice with water. After the dichloroethane has been distilled off, 18 g of product remain. 94% purity according to GC analysis.

EXAMPLE A7

2-Chloro-3,5,6-trifluoro-4-nitrophenol

Analogously to Example A5, nitration of 28 g of 2-chloro-3,5,6-trifluorophenol gives 25 g of 2-chloro-3,5,6-trifluoro-4-nitrophenol, having a purity of 93% and a melting point of 107°-109° C.

EXAMPLE A8

2,6-Dichloro-3,5-difluoro-4-amino-phenol 18 g of 2,6-dichloro-3,5-difluoro-4-nitrophenol are hydrogenated in 100 ml of methanol in the presence of 1.5 g of Raney nickel at 25°-45° C. and 30-50 bar of hydrogen, until hydrogen is no longer taken up. After filtration, the solution is freed from the solvent under reduced pressure. 13 g of aminophenol remain (GC purity 98.4%); m.p. 151° C.

EXAMPLE A9

2-Chloro-3,5,6-trifluoro-4-amino-phenol

Analogously to Example A8, hydrogenation of 25 g of 2-chloro-3,5,6-trifluoro-4-nitro-phenol in 120 ml of methanol and 2 g of Raney nickel gives 20 g of aminophenol (GC purity 97%).

The following compounds of the formula (IV) are obtained analogously to Example A1.

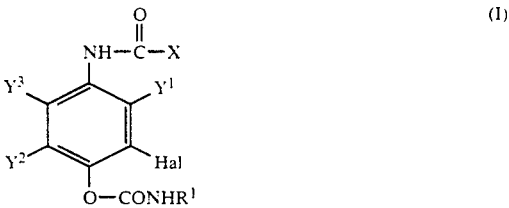

| Example No. | X' | Y¹ | Y³ | Y² | Hal |
|---|---|---|---|---|---|
| A11 | cyclohexenyl-CH₃ | Cl | H | H | Cl |
| A12 | cyclohexenyl-CH₃ | Cl | H | Cl | H |
| A13 | cyclohexenyl(CH₃)(CH₃) | Cl | H | H | Cl |
| A14 | CH₃-cyclohexenyl(CH₃)(CH₃) | Cl | H | H | Cl |
| A15 | CH₃-cyclohexenyl(CH₃)(CH₃) | Cl | H | Cl | H |
| A16 | cyclohexenyl(CH₃)(CH₃) | Cl | H | Cl | H |

EXAMPLE

Botrytis Test (Bean)/Protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, a clearly high activity is shown, for example, by the compounds of the following Preparation Examples: 1, 7, 10., 11, 13 and 14.

It is understood that the specification and examples are illustrative but not limitative of the present invention and that other embodiments within the spirit and scope of the invention will suggest themselves to those skilled in the art.

We claim:

1. A cycloalkyl-carboxanilide carbamate of the formula $$\text{(I)}$$

in which

X represents optionally alkyl-substituted cycloalkyl,
Hal represents halogen, and
$Y^1$, $Y^2$ and $Y^3$ independently of one another represent hydrogen, halogen, optionally halogen-substituted alkyl, optionally halogen-substituted alkoxy or optionally halogen-substituted alkylthio, and at least one of $Y^1$, $Y^2$ and $Y^3$ represents halogen, and
$R^1$ represents optionally halogen-substituted alkyl, alkenyl, alkylcarbonyloxyalkyl, alkenylcarbonyloxyalkyl and optionally substituted cycloalkyl, which can be interrupted by hetero atoms, or represents optionally substituted phenyl or optionally substituted phenylalkyl.

2. A compound according to claim 1, in which
X represents cyclopropyl, cyclobutyl, cyclopentyl, cyclohexyl or cycloheptyl, each of which is optionally monosubstituted or hexasubstituted by identical or different substituents from the group consisting of straight-chain or branched alkyl radicals having 1–4 carbon atoms,
Hal represents fluorine, chlorine or bromine,
$Y^1$, $Y^2$ and $Y^3$ are identical or different and represent hydrogen, fluorine, chlorine, bromine, straight-chain or branched alkyl having 1–4 carbon atoms, straight-chain or branched alkoxy or alkylthio each having 1–4 carbon atoms, or represent halogenoalkyl, halogenoalkoxy or halogenoalkylthio each having 1–4 carbon atoms in the straight-chain or branched alkyl moiety and 1–5 identical or different halogen atoms, and at least one of $Y^1$, $Y^2$ and $Y^3$ represents fluorine, chlorine or bromine, and
$R^1$ represents $C_1$–$C_8$-alkyl, $C_2$–$C_8$-alkenyl, $C_1$–$C_8$-alkylcarbonyloxy-$C_1$–$C_6$-alkyl or $C_2$–$C_8$-alkenylcarbonyloxy-$C_1$–$C_6$-alkyl, each of which is unsubstituted or monosubstituted to nonasubstituted by halogen, or represents $C_3$–$C_7$-cycloalkyl which is unsubstituted or monosubstituted to pentasubstituted by identical or different substituents from the group consisting of halogen, $C_1$–$C_4$-alkyl and $C_1$–$C_4$alkoxy, or represents phenyl which is unsubstituted or monosubstituted to pentasubstituted by identical or different substituents from the group consisting of $Y^{1'}$–$Y^{5'}$, or represents phenyl-$C_1$–$C_4$-alkyl which is unsubstituted or monosubstituted to pentasubstituted in the phenyl moiety by identical or different substituents from the group consisting of $Y^{1'}-Y^{5'}$, where $Y^{1'}-Y^{5'}$ are identical or different and have the meaning of $Y^1-Y^3$, $NO_2$ and cyano.

3. A compound according to claim 1, in which
X represents cyclopropyl, cyclobutyl, cyclopentyl, cyclohexyl or cycloheptyl, each of which is monosubstituted or disubstituted by identical or different substituents from the group consisting of straight-chain or branched alkyl radicals having 1–4 carbon atoms,
$Y^1$, $Y^2$ and $Y^3$ are identical or different and represent hydrogen, fluorine, chlorine, bromine, methyl or trifluoromethyl, and least one of $Y^1$, $Y^2$ and $Y^3$ represents fluorine, chlorine or bromine, and
Hal represents fluorine, chlorine or bromine, and
$R^1$ represents $C_1-C_6$-alkyl, $C_2-C_6$-alkenyl, $C_1-C_6$-alkylcarbonyloxy-$C_1-C_6$-alkyl or $C_2-C_6$-alkenylcarbonyloxy-$C_1-C_6$-alkyl.

4. A compound according to claim 1, in which
X represents cyclopentyl, cyclohexyl or cycloheptyl, each of which is substituted in the 1- or 1,3-position by methyl or ethyl, and each of which is optionally additionally substituted by a further alkyl radical having 1–3 carbon atoms,
Hal represents fluorine, chlorine, or bromine,
$Y^1$, $Y^2$ and $Y^3$ are identical or different and represent hydrogen, fluorine, chlorine, bromine, methyl or trifluoromethyl, and least one of $Y^1$, $Y^2$ and $Y^3$ represents fluorine, chlorine or bromine, and
$R^1$ represents $C_1-C_4$-alkyl, $C_2-C_5$-alkenyl or $C_1-C_5$-alkyl-carbonyloxy-$C_1-C_5$-alkyl.

5. A compound according to claim 1, wherein such compound is 2,3-dichloro-4-(1-methyl-cyclohexyl-carbonylamino)-phenyl N-methyl-carbamate of the formula

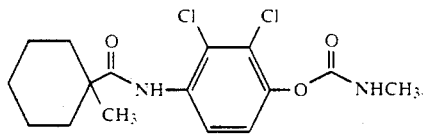

6. A compound according to claim 1, wherein such compound is 2,6-dichloro-4-(1-methyl-cyclohexyl-carbonylamino)-phenyl N-(2-acetoxy-propyl)-carbamate of the formula

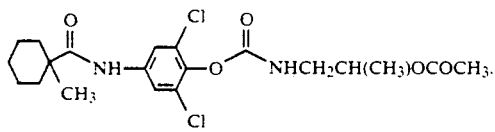

7. A compound according to claim 1, wherein such compound is 2,6-dichloro-4-(1-methyl-cyclohexyl-carbonylamino)-phenyl N-(2-t-butylcarbonyloxyethyl)-carbamate of the formula

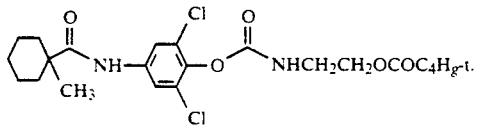

8. A compound according to claim 1, wherein such compound is 2,6-dichloro-4-(1-methyl-cyclohexyl-carbonylamino)-phenyl N-(2-acetoxyethyl)-carbamate of the formula

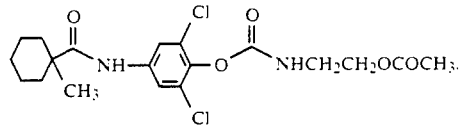

9. A compound according to claim 1, wherein such compound is 2,3-dichloro-4-(1-methyl-cyclohexyl-carbonylamino)-phenyl N-(2-butylcarbonyloxyethyl)-carbamate of the formula

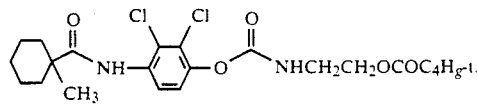

10. A fungicidal composition comprising a fungicidally effective amount of a compound according to claim 1 and a diluent.

11. A method of combating fungi which comprises applying to such fungi or to a fungus habitat a fungicidally effective amount of a compound according to claim 1.

12. The method according to claim 11, wherein such compound is
2,3-dichloro-4-(1-methyl-cyclohexylcarbonylamino)-phenyl N-methyl-carbamate,
2,6-dichloro-4-(1-methyl-cyclohexyl-carbonylamino)-phenyl N-(2-acetoxy-propyl)-carbamate,
2,6-dichloro-4-(1-methyl-cyclohexyl-carbonylamino)-phenyl N-(2-t-butylcarbonyloxyethyl)-carbamate,
2,6-dichloro-4-(1-methyl-cyclohexyl-carbonylamino)-phenyl N-(2-acetoxyethyl)-carbamate or
2,3-dichloro-4-(1methyl-cyclohexyl-carbonylamino)-phenyl N-(2-butylcarbonyloxyethyl)-carbamate.

13. A cycloalkenyl-carboxanilide carbamate of the formula

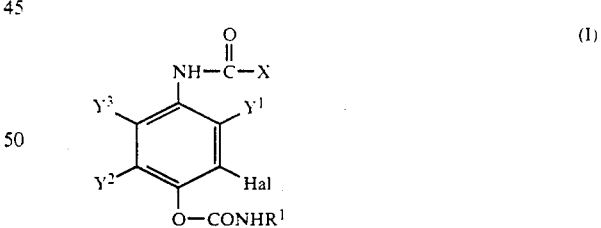

in which
X represents optionally alkyl-substituted cycloalkenyl,
Hal represents halogen, and
$Y^1$, $Y^2$ and $Y^3$ independently of one another represent hydrogen, halogen, optionally halogen-substituted alkyl, optionally halogen-substituted alkoxy or optionally halogen-substituted alkylthio, and
$R^1$ represents optionally halogen-substituted alkyl, alkenyl, alkylcarbonyloxyalkyl, alkenylcarbonyloxyalkyl and optionally substituted cycloalkyl which can be interrupted by hetero atoms, or represents optionally substituted phenyl or optionally substituted phenylalkyl.

14. A compound according to claim 1, in which

X represents cycloalkenyl having 5-7 ring members where the cycloalkenyl radical can be monosubstituted to hexasubstituted by identical or different substituents from the group consisting of straight-chain and branched alkyl radicals having 1-4 carbon atoms, Hal represents fluorine, chlorine or bromine.

$Y^1$, $Y^2$ and $Y^3$ are identical or different and represent hydrogen, fluorine, chlorine, bromine, straight-chain or branched alkyl having 1-4 carbon atoms, straight-chain or branched alkoxy or alkylthio each having 1-4 carbon atoms, or represent halogenoalkyl, halogenoalkoxy or halogenoalkylthio each having 1-4 carbon atoms in the straight-chain or branched alkyl moiety and 1-5 identical or different halogen atoms, and $R^1$ represents $C_1$–$C_8$-alkyl, $C_2$–$C_8$-alkenyl, $C_1$–$C_8$-alkylcarbonyloxy-$C_1$–$C_6$-alkyl or $C_2$–$C_8$-alkenylcarbonyloxy-$C_1$–$C_6$-alkyl, each of which is unsubstituted or monosubstituted to nanosubstituted by halogen, or represents $C_3$–$C_7$-cycloalkyl which is unsubstituted or monosubstituted to pentasubstituted by identical or different substituents from the group consisting of halogen, $C_1$–$C_4$-alkyl and $C_1$–$C_4$-alkoxy, or represents phenyl which is substituted or monosubstituted to pentasubstituted by identical or different substituents from the group consisting of $Y^1$–$Y^3$, or represents phenyl-$C_1$–$C_4$-alkyl which is unsubstituted or monosubstituted to pentasubstituted in the phenyl moiety by identical or different substituents from the group consisting of $Y^1$–$Y^3$, where $Y^1$–$Y^3$ are identical or different and have the same meaning of $Y^1$–$Y^3$, $NO_2$ and cyano.

15. A compound according to claim 1, in which

X represents cyclopentenyl, cyclohexenyl or cycloheptenyl, each of which is optionally monosubstituted or disubstituted by identical or different substituents from the group consisting of straight-chain or branched alkyl radicals having 1-4 carbon atoms, $Y^1$, $Y^2$ and $Y^3$ are identical or different and represent hydrogen, fluorine, chlorine, bromine, methyl or trifluoromethyl, and Hal represents fluorine, chlorine, or bromine, and $R^1$ represents $C_1$–$C_6$-alkyl, $C_2$–$C_6$-alkenyl, $C_1$–$C_6$-alkylcarbonyloxy-$C_1$–$C_6$-alkyl or $C_2$–$C_6$-alkenylcarbonyloxy-$C_1$–$C_6$-alkyl.

16. A compound according to claim 1, in which

X represents cyclopentenyl, cyclohexenyl or cycloheptenyl, each of which is substituted in the 1- or 1,3-position by methyl or ethyl, and each of which is optionally additionally substituted by a further alkyl radical having 1-3 carbon atoms, Hal represents fluorine, chlorine, or bromine, $Y^1$, $Y^2$ and $Y^3$ are identical or different and represent hydrogen, fluorine, chlorine, bromine, methyl or trifluoromethyl, and $R^1$ represents $C_1$–$C_6$-alkyl, $C_2$–$C_6$-alkenyl, $C_1$–$C_6$-alkylcarbonyloxy-$C_1$–$C_6$-alkyl.

17. A compound according to claim 13, wherein such compound is 2,3-dichloro-4-(1-methyl-cyclohex-3-enyl carbonylamino)-phenyl N-methyl-carbamate of the formula

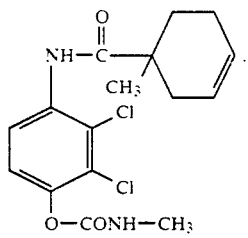

18. A compound according to claim 13, wherein such compound is 2,3-dichloro-4-(1,3-dimethyl-cyclohex-3-enyl carbonylamino)-phenyl N-methyl-carbamate of the formula

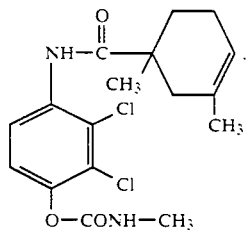

19. A compound according to claim 13, wherein such compound is 2,3-dichloro-4-(1,3,4-trimethyl-cyclohex-3-enyl carbonylamino)-phenyl N-methyl-carbamate of the formula

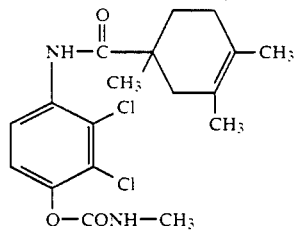

20. A fungicidal composition comprising a fungicidally effective amount of a compound according to claim 1 and a diluent.

21. A method of combating fungi which comprises applying to such fungi or to a fungus habitat a fungicidally effective amount of a compound according to claim 1.

22. The method according to claim 21, wherein such compound is 2-dichloro-4-(1-methyl-cyclohex-3-enyl carbonylamino)-phenyl N-methyl-carbamate, 2,3-dichloro-4-(1,3-dimethyl-cyclohex-3-enyl carbonylamino)-phenyl N-methyl-carbamate or 2,3-dichloro-4-(1,3,4-trimethyl-cyclohex-3-enyl carbonylamino)-phenyl N-methyl-carbamate.

* * * * *

UNITED STATES PATENT AND TRADEMARK OFFICE
CERTIFICATE OF CORRECTION

PATENT NO. : 5,176,914

DATED : January 5, 1993

INVENTOR(S) : Kruger et al.

It is certified that error appears in the above-identified patent and that said Letters Patent is hereby corrected as shown below:

| | |
|---|---|
| Col. 18, line 63 | After " $C_1$-$C_4$ " insert -- - -- |
| Col. 21, line 1 | Delete " claim 1 " and substitute -- claim 13 -- |
| Col. 21, lines 27-28 | Delete " substituted " and substitute -- unsubstituted -- |
| Col. 21, line 37 | Delete " claim 1 " and substitute -- claim 13 -- |
| Col. 21, line 51 | Delete " claim 1 " and substitute -- claim 13 -- |
| Col. 22, lines 49-50 | Delete " claim 1 " and substitute -- claim 13 -- |
| Col. 22, lines 53-54 | Delete " claim 1 " and substitute -- claim -- 13 -- |
| Col. 22, line 57 | Delete " 2-dichloro " and substitute -- 2,3-dichloro -- |

Signed and Sealed this

Fifth Day of July, 1994

Attest:

BRUCE LEHMAN

*Attesting Officer*    *Commissioner of Patents and Trademarks*